United States Patent [19]

Brandes et al.

[11] Patent Number: 4,478,848
[45] Date of Patent: Oct. 23, 1984

[54] COMBATING FUNGI WITH SUBSTITUTED ANILINOMETHYLENE-OXIMES

[75] Inventors: Wilhelm Brandes, Leichlingen; Werner Daum, Krefeld, both of Fed. Rep. of Germany

[73] Assignee: Bayer Aktiengesellschaft, Leverkusen, Fed. Rep. of Germany

[21] Appl. No.: 404,087

[22] Filed: Aug. 2, 1982

[30] Foreign Application Priority Data

Aug. 22, 1981 [DE] Fed. Rep. of Germany ....... 3133359

[51] Int. Cl.³ ..................... A01N 43/08; A01N 37/34; A01N 43/02; C07C 121/52
[52] U.S. Cl. ............................. 424/285; 260/465 E; 260/465 F; 260/465 D; 424/304; 424/278; 549/487
[58] Field of Search ........... 260/465 E, 465 F, 465 D; 424/304, 285, 278; 549/487

[56] References Cited

U.S. PATENT DOCUMENTS 4,305,887 12/1981 Herrling .......................... 260/465 E

FOREIGN PATENT DOCUMENTS 558336 1/1975 Switzerland ..................... 260/465 D
2029223 3/1980 United Kingdom ........... 260/465 D Primary Examiner—Henry R. Jiles
Assistant Examiner—Robert C. Whittenbaugh
Attorney, Agent, or Firm—Sprung Horn Kramer & Woods

[57] ABSTRACT

Substituted anilinomethylene-oximes of the formula

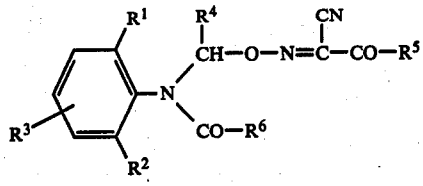

in which
$R^1$ denotes alkyl, alkoxy or halogen,
$R^2$ denotes hydrogen, alkyl or halogen,
$R^3$ denotes hydrogen, alkyl or halogen,
$R^4$ denotes hydrogen or methyl,
$R^5$ denotes alkoxy, amino or —NH—CO—NH—$R^7$,
$R^7$ represents hydrogen or optionally substituted alkyl, cycloalkyl or alkoxyalkyl, and
$R^6$ denotes alkoxy, alkoxycarbonyl, optionally substituted alkyl, alkenyl, alkynyl, cycloalkyl, aryl, aralkyl, oxyalkyl, arylthioalkyl or a heterocyclic radical or a heterocyclylalkyl group,
which possess fungicidal activity.

7 Claims, No Drawings

COMBATING FUNGI WITH SUBSTITUTED ANILINOMETHYLENE-OXIMES

The present invention relates to certain new substituted anilinomethylene-oximes, to a process for their production and to their use as plant protection agents.

As has been known for a long time, fungicides are used for plant protection in agriculture and horticulture: amongst the commercial fungicidal products, the compounds zinc ethylene-1,2-bis-dithiocarbamidate and N-trichloromethylthiotetrahydrophthalimide are of great importance (see R. Wegler, "Chemie der Pflanzenschutz—und Schädlingsbekämpfungsmittel" (Chemistry of Plant Protection and Pest-combating Agents), Volume 2, pages 65 and 108, Berlin/Heidelberg/New York (1970). However, the action of these compounds is not always completely satisfactory when low concentrations are used.

Furthermore, it is known that some isonitrosocyanoacetamide derivatives (see German Published Specification DOS No. 2,312,956, and U.S. Pat. Nos. 3,919,284, 3,957,847 and 4,188,401) and alkoxycarbonylethyl-N-haloacetylanilines (see German Published Specification DOS No. 2,350,944) have fungicidal properties. Even in the case of these compounds, the activity is not completely satisfactory when small amounts are used, and damage to plants is frequently observed when higher concentrations are used.

The present invention now provides, as new compounds, the substituted anilinomethylene-oximes of the general formula

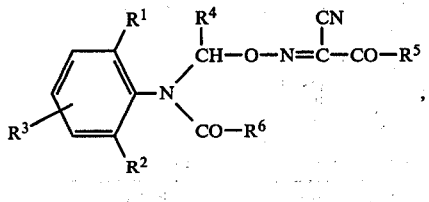

in which
R$^1$ denotes an alkyl or alkoxy group or a halogen atom,
R$^2$ and R$^3$ independently denote an alkyl group or a hydrogen or halogen atom,
R$^4$ denotes a hydrogen atom or a methyl group,
R$^5$ denotes an alkoxy, amino or —NH—CO—NH—R$^7$ group,
wherein
R$^7$ represents a hydrogen atom or an optionally substituted alkyl, cycloalkyl or alkoxyalkyl group, and
R$^6$ denotes an alkoxy, alkoxycarbonyl, optionally substituted alkyl, alkenyl, alkynyl, cycloalkyl, aryl, aralkyl, aryloxyalkyl or arylthioalkyl group, a heterocyclic radical or a heterocyclylalkylgroup.

The anilinomethylene-oximes according to the present invention of the general formula (I) can be present in various geometrical structures. All the isomers and mixtures thereof are the subject of the present invention.

According to the present invention we further provide a process for the production of a compound of the present invention, characterized in that, in a first step, an N-halogenoalkylaniline of the general formula

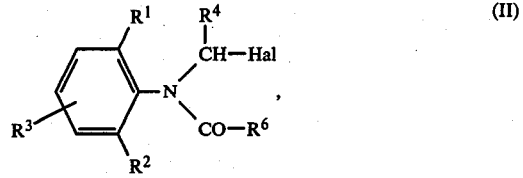

in which
R$^1$, R$^2$, R$^3$, R$^4$ and R$^6$ have the meanings given above and
Hal represents a leaving group, such as a chlorine, bromine or iodine atom,
is reacted with a 2-cyano-2-oximinoacetic acid derivative of the general formula

in which
R$^5$ has the abovementioned meaning,
in the presence of an acid-binding agent, or with an alkali metal or alkaline earth metal salt of the 2-cyano-2-oximinoacetic acid derivative of formula (III), if a compound according to the invention of the general formula

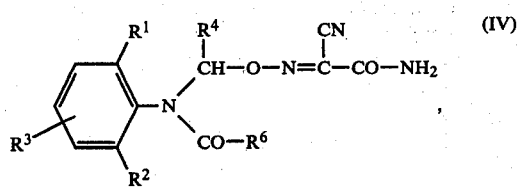

in which
R$^1$, R$^2$, R$^3$, R$^4$ and R$^6$ have the meanings given above, is produced, and a compound of formula (I) in which R$^5$ denotes an —NH—CO—NH—R$^7$ group is required, in a second step, the compound of formula (IV) is reacted with an isocyanate of the general formula

in which
R$^7$ has the meaning given above, other than a hydrogen atom,
in the presence of a base.

The new anilinomethylene-oximes of the present invention have powerful fungicidal properties. They can be used protectively, curatively and eradicatively. In addition, they have systemic and/or locosystemic properties. Surprisingly, they are better tolerated by plants than the known isonitrosocyanoacetamide derivatives. In comparison with the dithiocarbamidates and N-trichloromethylthio-tetrahydrophthalimide, they have the advantage of a curative and eridactive action.

Owing just to the many possible uses of their superior biological action, the compounds according to the invention represent a useful enrichment of the art. A further important aspect of this invention is that new active compounds having properties which are useful in practice are made available at a time when older active compounds are being removed from the market owing to signs of resistance.

Therefore, there is a definite need for new fungicides, today and in the foreseeable future.

Preferred anilinomethylene-oximes according to the present invention are those in which $R^1$ represents an alkyl or alkoxy group, each having 1 to 4 carbon atoms, or a halogen atom, $R^2$ and $R^3$ independently represent an alkyl group having 1 to 4 carbon atoms or a hydrogen or halogen atom, $R^4$ represents a hydrogen atom or a methyl group, $R^5$ represents an alkoxy group having 1 to 4 carbon atoms, an amino group or —NH—CO—NHR$^7$ wherein $R^7$ represents a hydrogen atom or an optionally substituted alkyl group having 1 to 5 carbon atoms or an alkoxyalkyl group having 2 to 5 carbon atoms, and $R^6$ represents an alkoxy group having 1 to 4 carbon atoms, an alkoxycarbonyl group having 1 to 4 carbon atoms, an optionally substituted alkyl group having 1 to 6 carbon atoms, an optionally substituted alkenyl group having 2 to 5 carbon atoms, an alkynyl group having 2 to 4 carbon atoms, a cycloalkyl group having 3 to 7 carbon atoms, an optionally substituted phenyl, benzyl, phenylethyl, phenoxymethyl, phenylthiomethyl or phenylthioethyl group or an optionally substituted, saturated or unsaturated heterocyclic radical or heterocyclylmethyl group, the heterocyclic structures thereof containing an oxygen or sulphur atom, up to three nitrogen atoms, or up to two nitrogen atoms and an oxygen or a sulphur atom as the heteroatoms.

Chlorine and bromine atoms may be mentioned as examples of halogen atoms.

Substituents of the radical $R^7$ are preferably cyano groups and alkoxycarbonyl groups having 1 to 4 carbon atoms.

If $R^6$ represents an alkylgroup, it can carry, as preferences, substituents such as alkoxy, alkylthio, alkylsulphonyloxy, alkylsulphoxy, alkylsulphonyl, alkoxyalkylthio, alkanoyloxy and alkoxyalkoxy, each having 1 to 4 carbon atoms in each alkyl part, propargyloxy, the cyano or thiocyanato group and halogen (such as fluorine, chlorine and bromine). If $R^6$ represents an alkenyl, alkynyl or cycloalkyl group, it can carry, as preferences, substituents such as halogen (for example fluorine, chlorine and bromine). If $R^6$ represents an aryl or aralkyl group, it can preferably carry up to three substituents, for example halogen (such as fluorine, chlorine and bromine), trifluoromethyl, cyano, nitro, alkyl and alkyl(thio)oxy, each having 1 to 4 carbon atoms, and methylenedioxy. If $R^6$ represents an aryloxymethyl or arylthioalkyl group, it can carry, as preferences, substituents such as halogen (for example chlorine) and alkyl (for example methyl and trifluoromethyl). If $R^6$ represents a heterocyclic radical or a heterocyclylalkyl group, it can carry, as preferences, substituents, for example alkyl (such as methyl and trifluoromethyl).

In addition to the compounds according to the invention mentioned in the preparative examples, the following further compounds according to the present invention, of the general formula (I), may be mentioned as examples:

TABLE 1

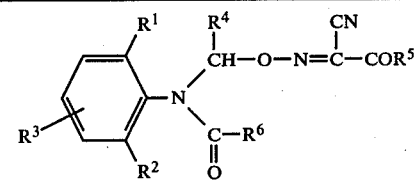

I

| $R^1$ | $R^2$ | $R^3$ | $R^4$ | $R^5$ | $R^6$ | $R^7$ |
|---|---|---|---|---|---|---|
| CH$_3$ | CH$_3$ | H | H | NHR$^7$ | CH$_2$Cl | CO—NH—C$_6$H$_{11}$ |
| CH$_3$ | CH$_3$ | H | H | NHR$^7$ | CHCl$_2$ | CO—NH—C$_6$H$_{11}$ |
| CH$_3$ | CH$_3$ | H | H | NHR$^7$ | CCl$_3$ | CO—NH—C$_6$H$_{11}$ |
| CH$_3$ | CH$_3$ | H | H | NHR$^7$ | CH$_2$CN | CO—NH—C$_6$H$_{11}$ |
| CH$_3$ | CH$_3$ | H | H | NHR$^7$ | CH$_2$SCN | CO—NH—C$_6$H$_{11}$ |
| CH$_3$ | CH$_3$ | H | H | NHR$^7$ | CH$_2$OCH$_3$ | CO—NH—C$_6$H$_{11}$ |
| CH$_3$ | CH$_3$ | H | H | NHR$^7$ | CH$_2$OC$_2$H$_5$ | CO—NH—C$_6$H$_{11}$ |
| CH$_3$ | CH$_3$ | H | H | NHR$^7$ | OCH$_3$ | CO—NH—C$_6$H$_{11}$ |
| CH$_3$ | CH$_3$ | H | H | NHR$^7$ | OC$_2$H$_5$ | CO—NH—C$_6$H$_{11}$ |
| CH$_3$ | CH$_3$ | H | H | NHR$^7$ | OCH(CH$_3$)$_2$ | CO—NH—C$_6$H$_{11}$ |
| CH$_3$ | CH$_3$ | H | H | NHR$^7$ | (furyl-methyl) | CO—NH—C$_6$H$_{11}$ |
| CH$_3$ | CH$_3$ | H | H | NHR$^7$ | CH$_2$OCH$_3$ | CO—NH—(CH$_2$)$_5$—COOCH$_3$ |
| CH$_3$ | CH$_3$ | H | H | NH$_2$ | CO—OC$_2$H$_5$ | — |
| C$_2$H$_5$ | CH$_3$ | H | H | NHR$^7$ | CH$_2$Cl | CO—NH—C$_4$H$_9$ |
| C$_2$H$_5$ | CH$_3$ | H | H | NH$_2$ | CH$_2$Cl | — |
| C$_2$H$_5$ | CH$_3$ | H | H | NH$_2$ | CH$_2$CN | — |
| C$_2$H$_5$ | CH$_3$ | H | H | NHR$^7$ | CH$_2$Cl | CO—NH$_2$ |
| C$_2$H$_5$ | CH$_3$ | H | H | NH$_2$ | CH$_2$Br | — |
| C$_2$H$_5$ | CH$_3$ | H | H | NHR$^7$ | CH$_2$Br | CO—NH$_2$ |
| C$_2$H$_5$ | CH$_3$ | H | H | NH$_2$ | CH$_2$—O—CH$_3$ | — |
| C$_2$H$_5$ | C$_2$H$_5$ | H | H | NHR$^7$ | CH$_2$Cl | CO—NH—CH$_3$ |
| C$_2$H$_5$ | C$_2$H$_5$ | H | H | NHR$^7$ | CH$_2$Cl | CO—NH$_2$ |
| C$_2$H$_5$ | C$_2$H$_5$ | H | H | NH$_2$ | CH$_2$Cl | — |
| C$_2$H$_5$ | C$_2$H$_5$ | H | H | NHR$^7$ | CH$_2$Br | CO—NH$_2$ |
| C$_2$H$_5$ | C$_2$H$_5$ | H | H | NH$_2$ | CH$_2$Br | — |

TABLE 1-continued $$\begin{array}{c} R^1 \quad R^4 \quad CN \\ \text{Ar-CH-O-N=C-COR}^5 \\ R^3-\text{Ar-N} \\ R^2 \quad C-R^6 \\ \parallel \\ O \end{array} \quad I$$

| $R^1$ | $R^2$ | $R^3$ | $R^4$ | $R^5$ | $R^6$ | $R^7$ |
|---|---|---|---|---|---|---|
| $C_2H_5$ | $C_2H_5$ | H | H | $NH_2$ | $CH_2CN$ | — |
| $C_2H_5$ | $C_2H_5$ | H | H | $NH_2$ | $CH_2SCN$ | — |
| $C_2H_5$ | $C_2H_5$ | H | H | $NH_2$ | $CH_2O-CH_3$ | — |
| $C_2H_5$ | $C_2H_5$ | H | $CH_3$ | $NH_2$ | $CH_2Cl$ | — |
| $C_2H_5$ | $CH_3$ | $CH_3$ | H | $NH_2$ | $CH_2OCH_3$ | — |
| $i\text{-}C_3H_7$ | $CH_3$ | H | H | $NH_2$ | $CH_2Cl$ | — |
| $i\text{-}C_3H_7$ | $CH_3$ | H | H | $NHR^7$ | $CH_2Cl$ | $CO-NH-C_2H_5$ |
| $i\text{-}C_3H_7$ | $CH_3$ | H | H | $NH_2$ | $CH_2Br$ | — |
| $i\text{-}C_3H_7$ | $CH_3$ | H | H | $NHR^7$ | $CH_2Br$ | $CO-NH-(CH_2)_5-CN$ |
| $t\text{-}C_4H_9$ | $CH_3$ | H | H | $NH_2$ | $CH_2Cl$ | — |
| $t\text{-}C_4H_9$ | $CH_3$ | H | H | $NHR^7$ | $CH_2Cl$ | $CO-NH_2$ |
| $t\text{-}C_4H_9$ | $CH_3$ | H | H | $NH_2$ | $CH_2Br$ | — |
| $t\text{-}C_4H_9$ | $CH_3$ | H | H | $NHR^7$ | $CH_2Br$ | $CO-NH-CH_3$ |

If N-chloromethyl-N-(2-ethoxyacetyl)-2,6-dimethylaniline and methyl 2-cyano-2-oximinoacetate are used as starting materials and N-ethyl-N,N-diisopropylamine is used as the acid-binding agent, the course of the first step of the reaction according to the present invention is illustrated by the following equation:

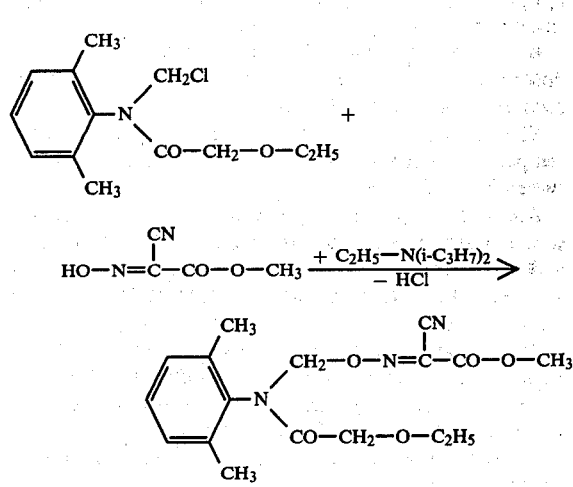

If 2-cyano-2-O-(N-(2,6-dimethylphenyl)-N-(furan-2-oyl)-aminomethyl)-oximinoacetamide, sodium hydride and n-propyl isocyanate are used as starting materials, the course of the second step of the reaction according to the present invention is illustrated by the following equation:

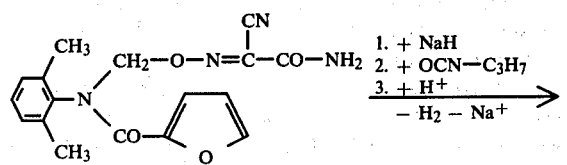

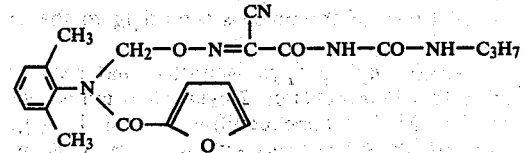

Preferred N-halogenoalkylanilines of formula (II) employed as starting materials are those in which the radicals $R^1$ to $R^4$ and $R^6$ have the meanings already mentioned in connection with the preferred compounds of formula (I).

N-Halogenoalkyl-anilines of the formula (II) which can be used according to the invention are known and can be prepared by processes which are known in principle, for example by the reaction of suitable anilines with aldehydes to give the Schiff bases, followed by reaction with acid halides (see U.S. Pat. Nos. 3,630,716 and 3,637,847; German Published Specifications DOS No. 1,542,950, 1,793,811, 2,854,598, 2,854,599 and 2,854,600; European Patent Application No. 29011 and Chemical Abstracts 64, 10760 g). Intermediate isolation of the N-halogenoalkyl-anilines of the formula (II) is not absolutely necessary.

The following may be mentioned as examples of anilines of formula (II):

N-bromoacetyl-N-bromomethyl-2,6-dimethylaniline; N-acetyl-, N-chloroacetyl-, N-dichloroacetyl-, N-trichloroacetyl-, N-2-cyanoacetyl-, N-2-methoxyacetyl-, N-2-ethoxyacetyl-, N-2-propoxyacetyl-, N-2-isopropoxyacetyl-, N-methoxyethyl-sulphonylacetyl-, N-ethoxyethylsulphenylacetyl-, N-propionyl-, N-2-chloropropionyl-, N-butanoyl-, N-methoxycarbonylacyl-, N-ethoxycarbonylacyl-, N-isopropoxycarbonylacyl-, N-butoxycarbonylacyl-, N-methoxycarbonyl-, N-ethoxycarbonyl- and N-isopropoxycarbonyl-N-chloromethyl-2,6-dimethylaniline and N-furanoyl-N-(1-chloroethyl)-2-chloro-6-methylaniline.

Furthermore, 2-cyano-2-oximinoacetic acid derivatives of the general formula (III) are required for the first step of the reaction according to the present invention. Some of these compounds are known (Chem. Ber. 42, 736–741 (1909); 54, 1334 (1921); and U.S. Pat. No. 4,188,401).

Thus, for example, an oximated urea of the general formula $$HO-N=\overset{CN}{C}-CO-NH-CO-NH-R^7, \quad (IIIa)$$

in which
R[7] has the meaning given in formula (I), with the exception of hydrogen,
is obtained when an isocyanate of the general formula $$R^7-NCO \quad (V)$$

in which
R[7] has the meaning given in formula (I), with the exception of hydrogen,
is reaction with ammonia, in a first step, to give N-substituted urea, and this product is reacted with cyanoacetic acid in a second step in the presence of acetic anhydride to give the corresponding 1-substituted 3-(2-cyanoacetyl)-urea, and this compound is reacted with nitrous acid to give the corresponding oximated urea.

Examples of oximated ureas or cyanoacetic acid derivatives of the formula (III) which can be employed in the first step of the process according to the present invention are:

methyl, ethyl, propyl, isopropyl and sec.-butyl 2-cyano-2-oximinoacetate; 2-cyano-2-oximinoacetamide; N[1]-(2-cyano-2-oximinoacetyl)-urea; and 1-(2-cyano-2-oximinoacetyl)-3-methyl-, -ethyl-, -propyl-, -isopropyl-, -butyl-, -isobutyl-, -amyl-, -ω-cyanoethyl-, -ω-cyanopentyl-, -ω-ethoxycarbonyl-methyl-, -ω-methoxycarbonylmethyl-, -ω-methoxycarbonylpentyl-, -methoxymethyl-, -3-methoxypropyl-, -cyclopropyl-, cyclopropylmethyl-, -cyclopentyl- and -cyclohexyl-urea.

Suitable diluents for the first step of the process according to the invention are any of the organic solvents which are inert to the reactants, preferably polar solvents (for example acetonitrile, acetone, chloroform, benzonitrile, dimethylacetamide, dimethylformamide, dimethylsulphoxide, chlorobenzene, ethyl acetate, dioxane, methyl ethyl ketone, methylene chloride and tetrahydrofuran) and non-polar solvents (for example toluene).

The reaction can also be carried out in a mixtures of water and a water-miscible organic solvent, or in heterogeneous systems consisting of water and a water-immiscible or partially water-miscible solvent.

Organic bases, preferably tertiary amines (for example quinoline, dimethylbenzylamine, N,N-dimethylaniline, ethyldicyclohexylamine, ethyldiisopropylamine, picoline, pyridine and triethylamine) are used as acid-binding agents, or the 2-cyano-2-oximinoacetic acid derivatives are employed in the form of their alkali metal or alkaline earth metal salts.

The reaction according to the invention is generally carried out at a temperature between $-50°$ and $80°$ C., preferably between $-30°$ and $40°$ C. When water is used, or used concomitantly, as the diluent, the reaction is carried out at a temperature between the solidification point of the aqueous solution and $+60°$ C., preferably between $0°$ and $+40°$ C.

The first step of the process according to the invention can be carried out, for example, as follows:

A 2-cyano-2-oximinoacetic acid derivative of the formula (III), dispersed or dissolved in a diluent, is initially introduced, and a molar amount of a tertiary amine is added, it being possible for salt formation to take place. If an alkali metal or alkaline earth metal salt of the 2-cyano-2-oximinoacetic acid derivative is employed, this can be initially introduced in an inert solvent. For this purpose, the N-halogenoalkylaniline, preferably dissolved in a diluent, is added. After the end of the reaction, the anilinomethyleneoximes are isolated in the customary manner and purified if appropriate.

In a particular procedure, a small amount of an iodide is added to the reaction mixture before the beginning of the reaction.

Anilinomethylene-oximes of the formula (IV) which are starting materials in the second step of the process according to the invention are compounds according to the invention. In formula (IV), the radicals R[1] to R[4] and R[6] preferably have the meanings mentioned in connection with formula (I) as being preferred.

In preferred isocyanates of formula (V) which are employed in the second step of the process according to the invention, R[7] has the meaning mentioned in connection with the preferred compounds of the present invention, with the exception of hydrogen.

The isocyanates of the formula (V) are known compounds. They can be prepared in a customary manner, for example by reacting primary amines with phosgene.

The following compounds of formula (V) may be mentioned individually:

methyl, ethyl, propyl, isopropyl, butyl, sec.-butyl, ω-cyanoethyl, 1-cyano-1-methyl-ethyl, ω-cyanopropyl, ω-cyanopentyl, methoxycarbonyl-methyl, ethoxycarbonyl-methyl, propoxycarbonyl-ethyl, 1-methoxycarbonyl-1-methyl-ethyl, 1-ethoxycarbonyl-1-methyl-ethyl, ethoxycarbonyl-1-ethyl-ethyl, methoxycarbonyl-1-ethyl-ethyl, methoxycarbonyl-propyl, methoxycarbonyl-pentyl, isopropoxycarbonyl-pentyl and cyclohexyl isocyanate.

Inert anhydrous solvents, such as ethers (for example diisopropyl ether, dioxane or tetrahydrofuran) can be used as diluents for the second step.

The reaction of the second step is carried out at a temperature between $-20°$ and $80°$ C., preferably between $20°$ and $60°$ C.

Alcoholates (for example alkali metal alcoholates, such as sodium methoxide and potassium tert.-butoxide) and metal hydrides (for example alkali metal hydrides, such as sodium hydride and potassium hydride) can be employed as bases.

The second step of the process according to the invention can be carried out, for example, as follows:

The 2-cyano-2-(N-acylanilino-alkoxyimino)-acetamide derivative of the formula (IV) in a diluent is reacted with an abovementioned base to give the corresponding anion of the amide, and this is reacted with the isocyanate of the formula (V) in the temperature range given. After the end of the reaction, the cold mixture is rendered slightly acidic with an organic carboxylic acid, such as acetic acid.

Depending on the reaction conditions, the active compounds according to the invention are precipitated as crystals, or remain dissolved in the organic solvent and, after washing the solution with water, can then be separated off by careful concentration of the solution or by the addition of a small amount of a weak polar organic solvent, such as cyclohexane, dibutyl ether, butyl acetate or carbon tetrachloride. If appropriate, water-miscible solvents must be removed after the reaction by evaporating them off in vacuo.

If the compounds according to the invention are dissolved in a water-miscible solvent, they can be precipitated, for example by the addition of water. If permitted by the particular conditions of the working-up processes, the solutions of the active compounds according to the invention, or the still solvent-moist suspensions of the active compounds, are rendered slightly acidic.

The compounds according to the present invention may decompose at a relatively high temperature.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Oomycetes, for example against the blight and late blight of potato and tomato causative organismen (*Phytophthora infestans*).

They exhibit a high curative and protective activity. In addition, good actions against rust fungi are found.

The active compounds according to the invention not only exhibit the good properties of outstanding commercial preparations, but possess in addition substantial advantages. These advantages lie in the main in the ability of the compounds according to the invention to penetrate into the plants. They can be taken up by the seed surface, by the roots and also by above-ground plant organs after external applications. In addition, they possess the advantageous ability of acting loco-systemically, that is to say, exercising an in-depth action in the plant tissue and thereby eliminating fungal pathogens which have already penetrated into the tissue of the host plant.

In order to broaden their spectrum of fungicidal action, to increase their activity and to delay the development of resistance, the compounds according to the invention can be applied together with known fungicidal active compounds.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.0001 to 0.02%, are generally required at the place of action.

The present invention also provides fungicidal composition containing as active ingredient a compound of the present invention in admixture with a solid or liquefied gaseous diluent or carrier or in admixture with a liquid diluent or carrier containing a surfaceactive agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

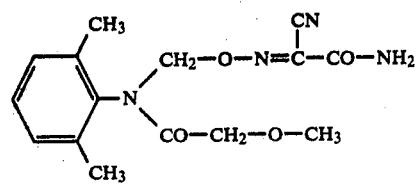

14.2 g (0.125 mol) of 2-cyano-2-oximinoacetamide and 250 ml of acetonitrile were introduced initially. 12.6 g of triethylamine were added dropwise while cooling with ice, followed by the addition, after half an hour, of a solution of 30 g (0.124 mol) of N-chloromethyl-N-methoxyacetyl-2,6-dimethylaniline in 400 ml of diisopropyl ether and 400 ml of toluene. The mixture was kept at 40° C. for 90 minutes. The reaction mixture was concentrated in vacuo, and the residue was washed with petroleum ether and with water. 27 g of 2-cyano-2-(O-(N-methoxyacetyl-N-2,6-dimethylphenyl-aminometh)-oximino)-acetamide, m.p. 173° to 174° C., were obtained.

The product melted at 174° to 175.5° C. after recrystallization from acetonitrile.

The following compounds were prepared in an analogous manner:

TABLE 2

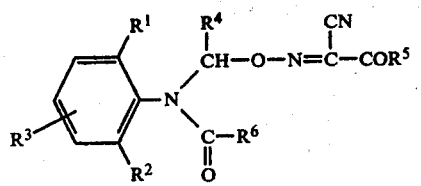

| Compound No. | $R^1$ | $R^2$ | $R^3$ | $R^4$ | $R^5$ | $R^6$ | Physical constants, m.p. °C. |
|---|---|---|---|---|---|---|---|
| 2 | $CH_3$ | $CH_3$ | H | H | $NHCONHR^7$ $R^7=H$ | $CH_2OCH_3$ | 156–160° C. |
| 3 | $CH_3$ | $CH_3$ | H | H | $NHCONHR^7$ $R^7=C_2H_5$ | $CH_2OCH_3$ | 113.5° C. |
| 4 | $CH_3$ | $CH_3$ | H | H | $NHCONHR^7$ $R^7=(CH_2)_5CN$ | $CH_2OCH_3$ | 136–138° C. |
| 5 | $CH_3$ | $CH_3$ | H | H | $NH_2$ | furyl | 184° C. |
| 6 | $CH_3$ | $CH_3$ | H | H | $NH_2$ | $CH_2Cl$ | 180° C. |
| 7 | $CH_3$ | $CH_3$ | H | H | $NHCONHR^7$ $R^7=C_2H_5$ | $CH_2Cl$ | 135° C. |
| 8 | $CH_3$ | $CH_3$ | H | H | $OCH_3$ | $CH_2-O-CH_3$ | 105° C. |
| 9 | $CH_3$ | $CH_3$ | H | H | $NH_2$ | $OCH_3$ | 187.5° C. |
| 10 | $CH_3$ | $CH_3$ | H | H | $NH_2$ | $CH_2SCN$ | IR ($CHCl_3$) 2160 cm$^{-1}$ |
| 11 | $CH_3$ | $CH_3$ | H | $CH_3$ | $NH_2$ | $CH_2Cl$ | 153° C. |
| 13 | $CH_3$ | $CH_3$ | H | H | $NH_2$ | $CH_2-S-CH_3$ | 133° C. |
| 14 | $CH_3$ | $CH_3$ | H | H | $NH_2$ | $CHCl-CH_3$ | 150° C. |

Example 2

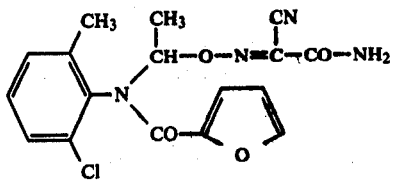

45.7 ml of acetaldehyde were added dropwise to a mixture of 73.6 g of 2-chloro-6-methylaniline, 403 ml of toluene, 0.5 ml of concentrated sulphuric acid and 86 g of zeolite at 3° C. in the course of 10 minutes. The mixture was stirred for 24 hours at 20° C. It was filtered and substantially concentrated in vacuo. The residue from evaporation was dissolved in 370 ml of toluene, and the solution was added dropwise to a solution of 33 g of furan-2-carboxylic acid-chloride in 200 ml of toluene at −30° C. After 3 hours, this reaction mixture was added to a mixture of 28.2 g of 2-cyano-2-oximino-acetamide, 200 ml of acetonitrile and 26 g of triethylamine which had been cooled to −30° C. The reaction mixture was left to stand overnight at room temperature. It was then filtered. The filtrate was concentrated in vacuo and the residue was treated with butyl acetate. 2-Cyano-2-(O-(1-(N-furan-2-oyl-N-2-chloro-6-methylphenyl-amino)-ethyl)-oximino)-acetamide crystallized out; m.p. 153° C.; Cl found 9.25 to 9.33% calculated 9.46%.

The fungicidal activity of the compounds of this invention is illustrated by the following biotest example.

In this example the compounds according to the present invention are each identified by the number (given in brackets) from Example 1 and Table 2.

Example 3

Phytophthora Test (tomato)/protective
Solvent: 4.7 parts by weight of acetone
Emulsifier: 0.3 part by weight of alkyl;aryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating has dried on, the plants were inoculated with an aqueous spore suspension of *Phytophthora infestans.*

The plants were placed in an incubation cabinet at 100% relative atmospheric humidity and at about 20° C.

Evaluation was carried out 3 days after the inoculation.

In this test, for example, a clearly superior activity compared with the prior art is shown by the compounds (1), (5) and (6).

It will be appreciated that the instant specification and examples are set forth by way of illustration and not limitation, and that various modifications and changes may be made without departing from the spirit and scope of the present invention.

We claim:

1. A substituted anilinomethylene-oxime of the formula

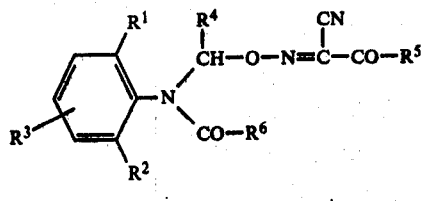

in which
$R^1$ represents an alkyl or alkoxy group, each having 1 to 4 carbon atoms, or a halogen atom,
$R^2$ and $R^3$ independently represent an alkyl group having 1 to 4 carbon atoms or a hydrogen or halogen atom,
$R^4$ represents a hydrogen atom or a methyl group,
$R^5$ represents an alkoxy group having 1 to 4 carbon atoms, an amino group or —NH—CO—NHR$^7$,
$R^7$ represents a hydrogen atom or an alkyl group having 1 to 5 carbon atoms and optionally substituted by cyano and/or alkoxycarbonyl having 1 to 4 carbon atoms, or an alkoxyalkyl group having 2 to 5 carbon atoms, and
$R^6$ represents an alkoxy group having 1 to 4 carbon atoms; an alkyl group having 1 to 6 carbon atoms and optionally substituted by alkoxy, alkylthio, alkylsulphonyloxy, alkylsulphoxy, alkylsulphonyl, alkoxyalkylthio, alkanoyloxy or alkoxyalkoxy, each having 1 to 4 carbon atoms in each alkyl part, propargyloxy, the cyano or thiocyanato group or halogen; an alkenyl group having 2 to 5 carbon atoms, an alkynyl group having 2 to 4 carbon atoms or a cycloalkyl group having 3 to 7 carbon atoms, each optionally substituted by halogen; a phenyl, benzyl or phenylethyl group optionally substituted by halogen, trifluoromethyl, cyano, nitro, methylenedioxy or alkyl, alkylthio or alkoxy each having 1 to 4 carbon atoms; a phenoxymethyl, phenylthiomethyl or phenylthioethyl group optionally substituted by halogen, trifluoromethyl or alkyl; or furyl or furfuryl optionally substituted by alkyl or trifluoromethyl.

2. A fungicidal composition comprising a fungicidally effective amount of a compound according to claim 1 in admixture with a diluent.

3. A method of combating fungi comprising applying to the fungi, or to a habitat thereof, a fungicidally effective amount of a compound according to claim 1.

4. A compound according to claim 1, wherein such compound is 2-cyano-2-(O-(N-methoxyacetyl-N-2,6-dimethylphenyl)-aminometh)-oximino)-acetamide of the formula

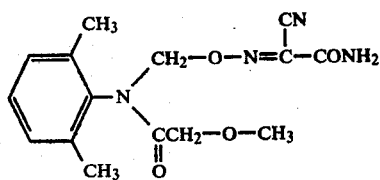

5. A compound according to claim 1, wherein such compound is 2-cyano-2-(O-(N-2-furoyl-N-2,6-dimethylphenyl-aminometh)-oximino)-acetamide of the formula

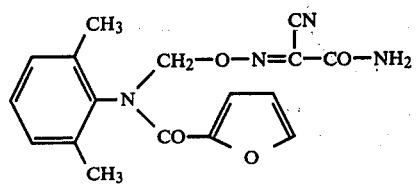

6. A compound according to claim 1, wherein such compound is 2-cyano-2-(O-(N-chloroacetyl-N-2,6-dimethylphenyl-aminometh)-oximino)-acetamide of the formula

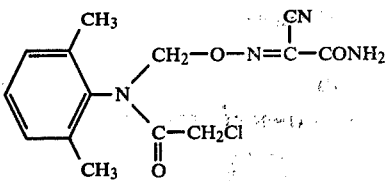

7. The method according to claim 3, wherein such compound is
2-cyano-2-(O-N-methoxyacetyl-N-2,6-dimethylphenyl-aminometh)-oximino)-acetamide,
2-cyano-2-(O-(N-2-furoyl-N-2,6-dimethylphenyl-aminometh)-oximino)-acetamide, or
2-cyano-2-(O-(N-chloroacetyl-N-2,6-dimethylphenyl-aminometh)-oximino)-acetamide.

* * * * *